United States Patent [19]

Duc

[11] 3,933,586

[45] Jan. 20, 1976

[54] METHOD OF MAKING L-ASPARTIC ACID FROM FUMARIC ACID

[75] Inventor: Nguyên-Công Duc, Nesle, France

[73] Assignee: Les Produits Organiques du Santerre Orsan, Paris, France

[22] Filed: Nov. 26, 1973

[21] Appl. No.: 418,863

Related U.S. Application Data

[63] Continuation-in-part of Ser. No. 394,868, Sept. 6, 1973, abandoned.

[30] Foreign Application Priority Data

Sept. 7, 1972 France .............................. 72.31655
Dec. 8, 1972 France .............................. 72.43684

[52] U.S. Cl. ...................... 195/65; 195/30; 195/47; 195/50
[51] Int. Cl.² ................. C12D 13/06; C12D 13/10
[58] Field of Search ...................... 195/30, 65, 66 R

[56] References Cited

UNITED STATES PATENTS 3,198,712  8/1965  Takahashi et al...................... 195/30

Primary Examiner—Lionel M. Shapiro

[57] ABSTRACT

The invention is concerned with a new microorganism, named PO 7111 strain belonging to the family of Pseudomonacea, and with a process of converting fumaric acid into L-aspartic acid using said microorganism. In a first step the microorganism is cultivated in aerobian conditions in a nutritive medium containing sources of carbon, phosphorus, nitrogen, and oligoelements and in a second step fumaric acid is introduced into said medium, the conversion being carried for 12–16 hours at a pH between 6 and 12 and at a temperature between 30° and 60°C.

22 Claims, No Drawings

3,933,586

METHOD OF MAKING L-ASPARTIC ACID FROM FUMARIC ACID

BACKGROUND

This application is a continuation-in-part of my application Ser. No. 394868 filed Sept. 6, 1973, and now abandoned.

The present invention has for its object an improved method of making aspartic acid by bio-conversion of fumaric acid.

The invention also relates to a new microorganism useful in particular for carrying out this method; moreover the inventiion relates to a process of production in situ of an amino-transferase, which involves the use of this microorganism, such an enzyme being able to convert fumaric acid into L-aspartic acid.

Numerous methods for preparing or isolating the aspartic acid from natural products have been described.

Among these methods, most of them use either hazardous and/or too costly raw materials, or complicated processes.

The methods using bio-conversion are the only ones allowing industrial applications. However, all methods disclosed heretofore show low reaction rates and they lead to a costly final product. This restricts their applications to pharmaceutical uses only.

The recent utilization of aspartic acid as a raw material for the synthesis of various peptides offers an interesting market to this amino-acid. But at the industrial scale, this utilization involves the obtainment of highly pure aspartic acid, with a low cost.

The microorganisms considered as being the best for producing the amino-transferase necessary to the conversion of fumaric acid into L-aspartic acid need for their growing, a complex culture medium containing in addition to a carbon providing material, organic nitrogen sources, which frequently are proteic hydrolyzates which are raw materials of variable composition and relatively high cost. As a consequence, the known methods using these microorganisms can be considered as being complex and poorly convenient for a large scale production. A known method using a microorganism of this kind and having the aforementioned drawbacks is described in the French patent No. 1,394,722 wherein the bio-conversion of fumaric acid is carried out by *Pseudomonas trifolii* developed on a glucose-peptone broth medium ("MIEKI"); moreover the conversion performed at 37° C and neutral medium is rather low.

The applicant has discovered a new microorganism of the Pseudomonacea family which avoids the aforementioned drawbacks. This microorganism can perform, by using simple means, the bio-conversion of non saturated organic acids, such as fumaric acid, into L-aspartic acid with reaction rates considerably higher than those corresponding to the methods known heretofore. The obtained yields are very high and the product can be easily extracted with a very high purity grade.

DESCRIPTION OF THE NEW MICROORGANISM OF THE INVENTION

The microorganism has been isolated in France at Nesle (Somme) from liquid effluents in the manufacture of beet sugar. It belongs to the Pseudomonas kind but is considered as new because it differs from bacteria of this type by one or several reproducible and constant features according to the criteria defined in "Bergey's Manuel" issued (1967). These features are the following:

rods: short, alone or by pairs, poorly or not mobile.
coloration of gram: negative
colonies:
  a. on gelose: round, whitish to light chamois, bright with translucent outlines, 3 mm diameter after four days of incubation at 30°C.
  b. on gelatine: round, whitish to yellow, bright smooth bulged.
injections into gelatine boss: no liquefaction
medium B of KING: production of fluorescent green dye non diffusible after 24 hours of incubation at 30°C.
milk: not becoming alkaline
nitrate: not reduced into nitrite
growth on glucose, lactose, sucrose, levulose, mannitol, glycerol, without acidification
tyrosine medium: no development
phenol: no reaction
no production of indole, sulphydric acid or gas.
no lysine decarboxylase
in aerobian conditions: good growth between 30° and 37° C.

The isolation of the microorganism can be effected in the following conditions and according to the usual techniques of isolation and purification.

Some samples of 0.1 ml of liquid effluent from a factory making sugar from sugar-beet are spread onto a Petri dish containing a solid gelose medium A having the conventional following composition:

| | |
|---|---|
| Beef extract | 20 gr/l |
| Peptone | 20 gr/l |
| Glucose | 4 gr/l |
| NaCl | 5 gr/l |
| Gelose | 15 gr/l |

The incubation is carried out at about 30° C. After 24 to 30 hours of incubation many colonies are observed.

Each of them is treated to be purified by successive spreading on the said medium and according to the aforementioned conditions.

A microscopic observation is sufficient to check the morphological homogeneity of the bacteria for each isolated and purified Pseudomonas colony.

The strains thus obtained in the form of a pure culture are kept on the abovementioned medium A, in a slant.

The strains are further tested to determine their capacity to produce the L-aspartic acid by means of a culture in a substrate containing fumaric acid. The following comparative table shows the capacity of producing three strains of Pseudomonas isolated during the same screening.

| Time of culture of the microorganism (hours) | 14 | | | 18 | | | 24 | | |
|---|---|---|---|---|---|---|---|---|---|
| Fumaric acid content at 0 hour of bioconversion (gr/l) | 36 | 115 | 178 | 36 | 115 | 178 | 36 | 115 | 178 |
| Percent of bioconversion after five days of bioconversion (%) strain: | | | | | | | | | |
| PO 205 | 0 | 0 | 0 | 0 | 1 | 1 | 1 | 1.2 | 1 |
| PO 7111 (invention) | 1 | 4 | 7 | 3 | 5 | 6 | 3 | 6 | 7 |
| PO 91 | 0 | 0 | 0 | 0 | 0 | 0 | 0 | 0 | 0 |

The Pseudomonas PO 7111 strain is confirmed as being by far the most productive. Consequently, samples thereof have been deposited at the American Type Culture Collection, Rockville, Md., ATCC Number 21973.

Unlike the other microorganisms known heretofore and used as producing amino-transferase, this strain can grow in a common medium comprising essentially for example extraction residues of sugar, i.e. molasses of sugar — beet or — cane, which residues are provided with a supplement of mineral phosphorus, for instance in the form of phosphate or phosphoric acid, and of nitrogen, for instance in the form of urea or ammonia, and some oligo-elements.

STUDY OF THE SPECIFICITY OF A NUTRITIVE MEDIUM

Applicant has been able to prove that the aforementioned medium with the said molasses remarkably promoted the formationn of amino-tranferase by the microorganism, although the mechanism of this process is not yet known.

Thus, the following example shows the specificity of the strain for such a medium. The measure thereof is carried out on the one hand by the quantitative determination of the specific enzyme in the medium, and on the other hand, by the measure of the conversion rate:

Fumaric acid — L-aspartic acid

EXPERIMENT NO. 1

Two culture media having the following features are prepared:

Artificial medium (Medium 1)

| | |
|---|---|
| glucose | 60 gr/l |
| Corn steep liquor | 40 gr/l |
| Mg SO$_4$, 7H$_2$O | 0.5 gr/l |
| Mono-potassic phosphate | 5 gr/l |
| fumaric acid | 1 gr/l |

Molasses containing medium (Medium 2)

| | |
|---|---|
| Molasses (in terms of total sugar) | 60 gr/l |
| monopotassic phosphate | 5 gr/l |
| Mg SO$_4$, 7H$_2$O | 0.5 gr/l |
| urea | 8 gr/l |

After sterilization of the medium by heating during 20 minutes at 121° C, the pH value is adjusted from 7 to 7.2 with gaseous ammonia, under sterile conditions.

Each medium is then inoculated with the PO 7111 strain in a saline suspension. The culture is carried out on a rotative agitator in 6 liter flasks containing 1 liter of the medium.

The bacteria development is evaluated by measurement of the optical density, after dilution to a twentieth, and the amino-transferase activity is measured according to the method disclosed in "Methods in Enzymology".

| Fermentation time (hours) | MEDIUM 1 | | MEDIUM 2 | |
|---|---|---|---|---|
| | Population in bacteria/ml | Activity expressed in international amino-transferase units/1/hour | Population in bacteria/ml | Activity expressed in international amino-transferase units/1/hour |
| 0 | 1 × 10$^8$ | — | 1 × 10$^8$ | — |
| 10 | 0.8 × 10$^9$ | 18.8 | 0.9 × 10$^9$ | 26 |
| 15 | 1 × 10$^{10}$ | 18 | 0.9 × 10$^{10}$ | 24 |
| 20 | 1.1 × 10$^{10}$ | 19 | 1.1 × 10$^{10}$ | 32.6 |
| 24 | 1.1 × 10$^{10}$ | 18.8 | 1.0 × 10$^{10}$ | 31.2 |

It is observed that if the bacteria development is nearly the same in both media, the amino-transferase activities are higher by 50 to 60 % when the microorganism is cultivated in the medium No. 2.

More generally, the most appropriate nutritive medium for the amino-transferase production and consequently for the conversion of the fumaric acid is, according to the present invention, a medium which has substantially the following composition:

- 15 to 60 gr/l of molasses (in terms of total sugar) preferably 40 gr/l expressed in total sugar.
- 1 to 4 gr/l of phosphoric acid or mineral phosphates (expressed in phosphoric acid quantities), preferably 2 to 2.6 gr/l.
- 0.1 to 1 gr/l of Mg (expressed in MgSO$_4$) preferably 0.4 to 0.6 gr/l of Mg SO$_4$.
- 0.5 to 10 gr/l of fumaric acid, preferably 0.9 to 1.1 gr/l.

The pH of the resulting aqueous medium is adjusted between 7 and 8.5, preferably at about 7.

During the culture whose duration is between 9 and 15 hours, preferably between 10 and 12 hours, the temperature should not be higher than 38°C.

In the same way, the growth of the microorganism is prevented if the temperature becomes lower than 25° C. An optimal density of population is obtained at 30° C.

Traces of oligo-elements can be added within a range of 0 to 10 ppm, either by incorporating same to the culture medium in the form of mineral salts, or by using tap water which is not demineralised so as to adjust the volume of the medium to one liter.

INFLUENCE OF THE MEDIUM PHYSICO-CHEMICAL CONDITIONS

The microorganisms used heretofore had such characteristics that the enzyme secreted by same was thermolabile and very sensitive to the physico-chemical conditions of the bio-conversion medium, especially to the pH and temperature.

The systematic study of the PO 7111 strain shows that this microorganism could accumulate in a culture medium mainly containing molasses, an enzyme whose activity covers a very wide field of operating conditions for the bio-conversion of fumaric acid, more particularly conditions concerning temperature and pH values.

Thus, the different measurements effected show that the culture of the PO 7111 strain on the molasses containing medium leads to the obtainment of a medium containing the enzyme which operates the fumaric acid amination into L-aspartic acid in such conditions that the enzyme activity increases with the conversion temperature increase, and that within a large temperature range from 20° to 60° C; in the same way, the increase of the bio-conversion pH has been observed to have a favourable influence on the transformation rate in a pH range from 6 to 12.

In order to study the influence of these two parameters up on the bio-conversion rate, the PO 7111 strain was cultivated in the molasses containing medium described in the aforementioned experiment No. 1 ; 10 liters of this medium are thus prepared for each of the two experiments described below.

EXPERIMENT NO. 2

Influence of the temperature upon the Bio-conversion Rate 2 kg of ammonium fumarate is added to the previously prepared 10 liter culture, after adjusting the pH to 8 and the temperature to the selected value. During the conversion, the pH is kept to 8 by adding gaseous $NH_3$.

The activity is measured by quantitative analysis according to the method described in "Methods in Enzymology" Volume 13, after a reaction time of 1 hour with stirring, and then again after each following hour during 4 hours. The data given in the table correspond to the average values of the so performed five measurements:

| Bio-conversion temperature (° C) | 20 | 30 | 37 | 40 | 50 | 57 | 60 |
|---|---|---|---|---|---|---|---|
| Amino-transferase activity in millimoles/liter/hour | 0.01 | 0.05 | 0.07 | 0.08 | 0.12 | 0.14 | 0.14 |

The activity is observed as increasing almost linearly where the bio-conversion temperature raises from 20° to 50° C, then more slowly between 50° and 60° C, but also it does not become null at 60° C.

According to the invention, the bio-conversion will be then achieved between 30° and 60° C, but preferably between 50° and 60° C, and more specifically between 55° and 57° C, since the optimum temperature seems to be about 55°–57° C.

EXPERIMENT NO. 3

Influence of the pH upon the Bio-conversion Rate

One operates with fractions of the same molasses containing medium as in Experiment No. 2. The 10 liter fractions are being poured in a tank provided with an agitator and maintained at 57° C. After an addition of 2 kg of diammonium fumarate the bio-conversion rate is followed in the same manner as in Experiment No. 2.

The data indicated in the following table show the average of 5 successive measurements performed as explained in Experiment No. 2.

| pH of the medium during bio-conversion | 7 | 7.5 | 8 | 8.5 | 9 | 9.5 | 10 |
|---|---|---|---|---|---|---|---|
| Amino-transferase activity in millimoles/liter/hour | 0.07 | 0.11 | 0.22 | 0.30 | 0.32 | 0.34 | 0.34 |

It is to be noted that the medium has a tendency to evolve gaseous ammonia when the pH is higher than 8.75, and that it is preferable to keep the tank under slight pressure in order to avoid losses.

The results show that the rate increases proportionally when the pH raises from 7 to 8.75, then more slowly between 8.75 and 9.50 and finally becomes constant above the 9.50 value. According to the present invention, the bio-conversion is consequently performed at a pH between 8.5 and 10, and preferably between 9 and 9.5.

Moreover, the study of the influence of the concentration of the substrate to be transformed, namely the fumaric acid, shows that the conversion rate appears to be the best when the fumaric acid content is about 10 % in the medium, but this rate is not affected by the content of the formed L-aspartic acid (within the saturation limits of the solution). It is then desirable to perform the process by successively adding some quantities of substrate in order to maintain the fumaric acid concentration at about 10 % as long as possible. However, in order to avoid having a too important quantity of non converted reagent in the solution used for the aminoacid extraction, the feeding is stopped during the last hours of the operation.

According to a preferred embodiment of the invention, the production of the amino-transferase necessary to the bio-conversion is carried out by aerobian incubation of the PO 7111 strain in a culture medium containing sugar-beet or sugar-cane molasses as the only carbon providing material, and a limited fumaric acid amount as an effective agent for the amino-transferase accumulation by this microorganism.

When the optimum percentage is obtained, the culture is stopped and then put into contact with the substrate, so that the last one would be transformed into aspartic acid.

The enzyme activity is not affected by the presence of other microorganisms; as a consequence it is not necessary to work in a sterile medium at the time of the bio-conversion of fumaric acid into L-aspartic acid.

It is then possible to use a substrate without special treatment thereof and in particular pure crystallized fumaric acid such as found on the market; a fumarate can also be employed.

The solid is then added, without previous sterilization, to the bio-conversion medium so as to maintain therein a concentration of about 10 %.

This bio-conversion phase is carried out without aeration in order to avoid undesirable by-products formation, especially oxidation products of ethylenic acid. The implied reagent is the diammonium fumarate whether fumaric acid is poured into the ammoniacal syrupy residual medium.

The reaction is performed in presence of an inert gas such as nitrogen.

During the conversion, the temperature is preferably kept to 55°-57° C and the pH adjusted to 9-9.5 by addition of gaseous ammoniac.

At the end of the reaction, namely when the residual fumaric acid percentage has been reduced to values such as the yield is maximum, the reactive mixture is submitted to a separation by usual and known per se means, such as centrifugation, filtration etc. . . , in order to remove therefrom microorganisms and any other insoluble compounds.

Thus, a concentrated solution of aspartic acid is obtained and the amino-acid is extracted from same by using conventional means such as insolubilization when the pH takes a value equal to that of the isoelectric point.

The resulting crystallized product obtained according to the invention conditions has a sufficiently great purity for industrial uses, but can be furthermore purified to obtain a product satisfying to the pharmaceutical standards by a mere recrystallization treatment after discoloration.

Non limitative examples of the present invention are given herebelow.

EXAMPLE 1

The optimal bio-conversion conditions which are specific to the PO 7111 strain have been applied on the industrial scale during operations carried out in an apparatus allowing obtainment of 1m3 of culture with a high concentration in amino-transferase.

Preparation of the Culture

In a fermentation apparatus fitted with a stirrer and heating means, 1000 liters of a medium having the following composition is prepared:

| | |
|---|---|
| molasses | 40 gr/liter expressed in total sugar quantity |
| phosphoric acid | 2.3 gr/liter |
| magnesium sulfate | 0.5 gr/liter |
| fumaric acid | 1 gr/liter |
| distilled water | qsp 1 liter |

The pH is adjusted to 7 with ammonia before sterilization. The latter is obtained by heating at 123° C during 30 minutes.

The medium thus prepared is inoculated with a 20 liter preculture of Pseudomonas (PO 7111 strain).

The culture is being developed in a sterile medium and under controlled conditions of temperature with stirring and aeration.

The operating conditions are the following:
Temperature: 30° C
Stirring: 100 r.p.m.
Aeration rate: 0.8 volume per volume per minute After a culture period of 11 hours, the bacteria population has reached $10^{10}$ bacteria/ml. and the pH is 8.95. The enzymatic activity is then maximum.

Bioconversion

At the end of the culture period, the fermentation apparatus is opened to the air and the agitation is stopped. The temperature is progressively increased to 55°-57° C while maintaining stirring, and the substrate is then progressively added by pouring crystallized fumaric acid directly into the tank, and this until a concentration of 100 gr/liter is obtained. The pH of the medium is maintained between 8.9 and 9.1 by adding gaseous ammonia.

The conversion is observed by measurement of the formed L-aspartic acid. The addition of fumaric acid is adjusted so as to keep the concentration thereof at about 10 %.

The operation goes on during 12 hours, then the addition of fumaric acid is decreased while maintaining the temperature and pH. The content is thus lowered until the 15th hour, and, at this time, the medium contains 180 gr/liter of L-aspartic acid and 30 gr/liter of non converted fumaric acid. The addition of fumaric acid is then stopped. The total amount of added substrate is equal to 160 kg. The stirring is continued while maintaining the temperature and pH until the 20th hour.

At this moment, the L-aspartic acid content in the medium raises to 21.1%. and that of the residual fumaric acid raises to 0.7 %. Consequently, a fumaric acid amount of about 155 kg has been converted with a yield of 109 %, corresponding to a molar yield of 95 %. The aspartic acid can be extracted according to example 2 or example 3.

EXAMPLE 2

The solution of example 1 is treated in view of the extraction of the crystallized L-aspartic acid. For this purpose, an acidification of the solution is practiced and the pH thereof is adjusted to 5.8 by concentrated hydrochloric acid ; then the temperature is increased to about 53°-55° C and a 10 gr/liter solution of a flocculating agent of the sulfonated polystyrene type is added. After a 15 minute contact time, the insoluble parts and flocculated materials are taken away by filtration under vacuum with a drum-filter coated with a layer of expanded perlite (Trade Mark : "Decalite"). The filtration rate is 500 liter/m²/ hour. The filtered solution is fully clear. Then it is cooled down to a temperature of 30° C and, while stirring, it is becoming acid by pouring concentrated hydrochloric acid to a pH value of 2.8-3. After 8 hours, the crystals can be extracted from the mother liquor, and they are dryed by centrifugation.

The purity degree of the water-washed crystals is better than 99 %. 183 kg of L-aspartic acid are thus obtained.

EXAMPLE 3

10 m³ of the solution resulting from bioconversion of the fumaric acid into L-aspartic acid and obtained according to example 1 is treated for the extraction of the amino-acid. For this purpose, the pH is adjusted to 5.8 by the addition of sulfuric acid in the proportion of 60 % by weight.

At the same time, the temperature is being increased up to about 55° C. Then, a floculating agent of the sulfonated polystyrene type is added in the form of a 10 gr/liter aqueous solution. The now employed floculating agent is known under the trade mark "Purifloc A-21". 0.5 gr of this product is used for each liter of solution to be treated.

After a 15 minute contact time, the microorganisms, cellular fragments, floculated colloids and other insoluble impurities are separated by means of a plate separator of the "skimmer" type. The separation is excellent because the turbidity of the clear phase is equal to 25° Kaolin instead of more than 5000° Kaolin before treatment.

The Kaolin degree is remembered as being the turbidity corresponding to the suspension of 1 mg of Kaolin in one liter of water. Then a fraction of 0.5% by weight is taken away as being slimes containing only a very low aspartic acid percentage. The clear solution is further purified by adding some active coal and filtration additive.

The 10 m³ solution containing 200 gr per liter of aspartic acid is thus added with 30 kg of active coal (trade Mark :SA 1635) and 50 kg of "Dicalite".

After a contact time of 30 minutes under slow stirring, the suspension is filtered on press-filter or drum-filter under vacuum while keeping the temperature constant. The filtration is very fast, the average rate being of 1 m3/m2/hour.

The solution thus obtained is quite clear and has a slight pale yellow coloration.

The L-aspartic acid is then crystallized by addition of 60 % sulfuric acid. This operation is carried out in a continuous manner in a group of stirred tanks arranged in series wherein the crystal slurry runs over from one tank to another. Some amounts of sulfuric acid are continuously added to each tank so that the pH variation is linear from the first tank to the last one. In this latter tank, the pH is adjusted to 2.8–3.

During crystallization, the tanks are cooled so as to keep the temperature at about 42°–45° C.

The complete crystals extraction out of the cleared solution is performed in a batch way by mixing at 20° C during 8 hours into a special tank provided with a stirring and cooling device.

The resulting mixture thus obtained is submitted to a liquid-solid drying separation step by means of a basket centrifugation apparatus.

The crystals are washed with soft water before drying. 180 kg of L-aspartic acid crystals with a purity grade of 97.5 to 98 % are obtained.

The product contains no fumaric acid, but only some mineral salts, in particular ammonium sulfate.

The latter can be easily removed by carrying out again a suspension in acidified water and by separating of the crystallized amino-acid.

The product such as obtained, without further washing, is pure enough to be used for the synthesis of peptides in general and sweetening dipeptides in particular.

Of course, the invention is by no means limited to the forms of embodiment described and illustrated, which have been given by way of example only. In particular, it comprises all the means constituting technical equivalents to the means described as well as their combinations, should the latter be carried out according to the spirit of the invention.

What is claimed is:

1. A method of production insitu of an amino-transferase which is non thermolabile and has little sensitivity to the physical-chemical conditions of the conversion media and being able to transform furmaric acid into L-aspartic acid at a high rate, comprising cultivating under aerobic conditions Pseudomonas PO 7111 (ATCC No. 21973) in a nutritive medium containing a source of carbon, a source of phosphorous, a source of nitrogen and oligo-elements.

2. A method according to claim 1, wherein said source of carbon is sugar-beet or sugar-cane molasses.

3. A method according to claim 1, wherein said nutritive medium comprises the following composition:
   molasses (expressed in total sugar amount): 15 to 60 gr/l, preferably 35 to 40 gr/l.
   phosphoric acid or mineral phosphates (in terms of phosphoric acid): 1 to 4 gr/l
   magnesium (in terms of sulfate): 0.1 to 1 gr/l
   oligo-elements: 0 to 10 ppm, its pH being adjusted between 7 and 8.5.

4. A method according to claim 1 wherein the phosphorous source is a compound selected from the group consisting of phosphoric acid and phosphoric acid salts of monovalent cations.

5. A method according to claim 1 wherein said nitrogen source is a substance selected from the group consisting of urea and ammonia.

6. A method according to claim 1, wherein said nutritive medium contains fumaric acid in a sufficient amount to allow accumulation of amino-transferase in the said medium.

7. A method of producing L-aspartic acid from a medium containing fumaric acid comprising preparing a culture of Pseudomonas R 7111 (ATCC No. 21973 under aerobic conditions, in a nutrient medium containing a carbon source, a phosphorous source, a nitrogen source and obligo-elements, to obtain a fermented medium rich in amino-transferase, comprising carrying out a bioconversion step by introduction of furmaric acid in said fermented medium, the bio conversion being carrried out without aeration at a pH between 6 and 12, and at a temperature between 30° and 60° and extracting the formed L-aspartic acid.

8. A method according to claim 7, wherein the bioconversion step is carried out when the concentration of the fermented medium in amino-transferase reaches about 30 international units per one milliliter of the said medium.

9. A method according to claim 7, wherein said carbon source is sugar-beet or sugar-cane molasses.

10. A method according to claim 9, wherein the bioconversion stage is effected after 12 to 16 hours of microorganism development.

11. A method according to claim 7, wherein the said nutritive medium has the following composition:
   molasses (expressed in total sugar): 15 to 60 gr/l, preferably 35 to 40 gr/l
   phosphoric acid or mineral phosphates (in terms of phosphoric acid): 1 to 4 gr/l
   magnesium (expressed in sulfate): 0.1 to 1 gr/l oligo-elements: 0 to 10 ppm, its pH being adjusted between 7 and 8.5.

12. A method according to claim 7, wherein the phosphorous source is monopotassic phosphate.

13. A method according to claim 7, wherein the nitrogen source is a compound selected from the group consisting of urea and ammonia.

14. A method according to claim 7, wherein the fumaric acid to be transformed is progressively introduced during the bioconversion stage.

15. A method according to claim 7, wherein the introducing rate of fumaric acid is adjusted during the bioconversion stage, in order to keep its concentration in the medium equal to about 10 %.

16. A method according to claim 7, wherein the pH is maintained between 8.5 and 10 during the bioconversion stage.

17. A method according to claim 7, wherein the temperature is kept between 55° and 57° C, during the bioconversion stage.

18. A method according to claim 7, wherein the pH is kept between 9 and 9.5 during the bioconversion stage.

19. A method according to claim 7, wherein the duration of the bioconversion stage is from about 15 to 20 hours.

20. A method according to claim 7, wherein the fumaric acid is introduced in the aforementioned medium in the form of the acid itself or in the form of salt.

21. A method according to claim 7, wherein the medium from the bioconversion is submitted to a floculating operation by addition of a floculating agent and to a subsequent separation operation of the insoluble compounds.

22. A method according to claim 21, wherein the limpid medium obtained from the said separation is added with concentrated sulfuric acid to a pH of approximately 3 so as to precipitate the L-aspartic acid, which is separated and washed with water to obtain a final product whose purity is about 97.5–98 %.

* * * * *